United States Patent
Schmatz

(10) Patent No.: US 8,728,394 B2
(45) Date of Patent: May 20, 2014

(54) DEVICE FOR STERILIZING CONTAINER CLOSURES

(75) Inventor: Stefan Schmatz, Bernhardswald (DE)

(73) Assignee: Krones AG (DE)

( * ) Notice: Subject to any disclaimer, the term of this patent is extended or adjusted under 35 U.S.C. 154(b) by 511 days.

(21) Appl. No.: 12/991,408

(22) PCT Filed: Apr. 30, 2009

(86) PCT No.: PCT/EP2009/055263
§ 371 (c)(1),
(2), (4) Date: Jan. 7, 2011

(87) PCT Pub. No.: WO2009/138326
PCT Pub. Date: Nov. 19, 2009

(65) Prior Publication Data
US 2011/0097239 A1 Apr. 28, 2011

(30) Foreign Application Priority Data
May 15, 2008 (DE) .......... 10 2008 023 797

(51) Int. Cl.
*A61L 2/00* (2006.01)
*A61L 2/10* (2006.01)
*A61L 2/08* (2006.01)

(52) U.S. Cl.
CPC ..... *A61L 2/10* (2013.01); *A61L 2/08* (2013.01)
USPC ............................................. 422/24; 422/22

(58) Field of Classification Search
CPC .................................. A61L 2/10; A61L 2/08
USPC ............ 422/291, 22, 24; 53/167; 250/455.11, 250/453.11
See application file for complete search history.

(56) References Cited

U.S. PATENT DOCUMENTS

| 2,095,502 | A | | 10/1937 | Johnston .......................... 21/54 |
| 3,105,720 | A | * | 10/1963 | Barker ............................ 406/88 |
| 3,170,231 | A | * | 2/1965 | Gleason ......................... 29/715 |
| 5,744,094 | A | | 4/1998 | Castberg et al. ............... 422/24 |
| 5,928,607 | A | | 7/1999 | Frisk ................................ 422/29 |
| 6,517,776 | B1 | | 2/2003 | Rodgers et al. ................. 422/24 |
| 6,683,312 | B2 | * | 1/2004 | Yun .......................... 250/455.11 |
| 2005/0013729 | A1 | * | 1/2005 | Brown-Skrobot et al. ...... 422/24 |
| 2006/0011263 | A1 | * | 1/2006 | Till ................................. 141/147 |
| 2009/0274576 | A1 | * | 11/2009 | Ressler ............................ 422/24 |

FOREIGN PATENT DOCUMENTS

| DE | 4407183 | 9/1995 | ............ B65B 55/08 |
| DE | 19520925 | 12/1996 | ............ B65B 55/00 |
| DE | 20201493 | 4/2003 | ............ G21K 5/04 |
| EP | 0277505 | 8/1988 | ............ A61L 2/10 |

(Continued)

OTHER PUBLICATIONS

International Search Report issued in Applicant's underlying PCT Application Serial No. PCT/EP2009/055263 dated Aug. 13, 2009, 3 pgs.

*Primary Examiner* — Regina M Yoo
(74) *Attorney, Agent, or Firm* — Hayes Soloway P.C.

(57) ABSTRACT

A device for sterilizing container closures includes a transport device which transports the container closures along a predetermined transport path (P), an enclosure, which surrounds the transport device at least in sections, and a light source, which applies ultraviolet radiation (S) to the container closures during the transport thereof along the transport path (P). The light source is disposed outside the enclosure, and the ultraviolet radiation is conducted into the interior of the enclosure.

20 Claims, 1 Drawing Sheet

(56) References Cited

FOREIGN PATENT DOCUMENTS

| | | | | |
|---|---|---|---|---|
| EP | 1518565 | 3/2005 | ................ | A61L 2/10 |
| EP | 1614630 | 1/2006 | .............. | B65B 55/08 |
| GB | 2364299 | 1/2002 | ................ | B67C 3/20 |
| WO | 92/18170 | 10/1992 | ................ | A61L 2/10 |
| WO | 99/12434 | 3/1999 | ................ | A23L 3/26 |
| WO | 01/17891 | 3/2001 | ................ | B67C 7/00 |
| WO | 02/36437 | 5/2002 | .............. | B65B 55/08 |
| WO | 03/021173 | 3/2003 | ................ | F26B 3/28 |

\* cited by examiner

DEVICE FOR STERILIZING CONTAINER CLOSURES

FIELD OF THE INVENTION

The present invention relates to an apparatus for sterilizing container closures and is suitable in particular for sterilizing closures for plastics-material or glass bottles.

BACKGROUND OF THE INVENTION

It is known from the prior art to fill containers, in particular under sterile conditions, with a beverage and then to close the containers with container closures. In this case care should also be taken that these container closures cannot contaminate the product itself. For this reason it is known to sterilize the closures before they are attached to the containers. One possibility of sterilization is for the closures to be acted upon with gas such as for example $H_2O_2$ vapour or with liquids such as disinfectants. For this type of sterilization, however, complicated conveying, sealing and handling devices are necessary. In addition, in processes of this type use is made of chemicals [which] are expensive, cannot generally be recycled, endanger the health of the user of the plant and have to be removed from the closures again at considerable expense. A further possibility of sterilization is for the container closures to be acted upon with sterilizing radiation, in particular ultraviolet radiation (UV radiation).

A sterilization apparatus is known from U.S. Pat. No. 2,095,502. In this case objects to be cleaned are subjected to a sterilizing light radiation. WO 01/17891 A1 describes an apparatus for filling containers, in which the closures are cleaned before entry into a clean room and in which the cleaning can also be carried out by means of a radiation device which emits UV radiation.

A method and an apparatus for sterilizing containers are known from DE 44 07 183 A1. In this case, containers are moved in a clock-timed manner in a pressure arrangement under a suitably arranged group of screened UV emitters which are permanently switched on. After that, the UV emitters are moved into the bottles, as a result of which an internal sterilization of these containers can be carried out and cleaning is then carried out again.

WO 02/36437 A1 describes methods and apparatus in which packages are subjected to UV radiation. WO 92/18170 discloses a sterilization method in which the material to be sterilized is subjected to UV radiation.

WO 03/021173 A1 describes a radiation apparatus for radiating articles with UV radiation, in which use is made of an elongate UV lamp for emitting UV radiation and an elongate reflector, in order to direct the radiation onto the containers. Apparatus of this type are applied in industrial use in the intended field of the apparatus according to the invention.

DE 202 01 493 U1 describes a radiation apparatus for irradiating an article with UV radiation in the ultraviolet or visible field. In this case one or more light-emitting diodes are used which illuminate the article to be irradiated.

A method and an apparatus for sterilizing containers with UV radiation are known from EP 1 614 630 A1. In this case in particular, the inner face of the container should be treated with UV radiation, in which case UV radiation from a UV source situated outside the container is introduced into the interior of the container.

In this case the apparatus known from the prior art have the problem that the light-generation source is frequently accessible only with difficulty since they take up space inside the plant. Since it is not possible for the UV sources, even in the event of a stoppage of the plant caused by a breakdown, to be switched off, the UV sources are in order to avoid a time-intensive restarting—as is known—provided with screening devices, so-called "shutters", which during the stoppage prevent the emission of radiation onto the articles to be irradiated. Without these screening devices the articles to be irradiated would be subjected to an excessively intensive radiation, since as a result of the stoppage of the plant they do not move past the radiation source but are stationary. On account of the afore-mentioned screening, a build-up of heat occurs in return inside the radiation source, and as a result a cooling device is necessary. These cooling devices are complicated and, in particular, are not desired in clean or sterile rooms since the hygienic status thereof is difficult to monitor and, in the case of cooling fans for example, undesired air swirling occurs in the sterile room. Although this cooling device is avoided by the apparatus disclosed in the afore-mentioned WO 01/17891 A1, complicated air locks and enclosed conveying devices are made necessary by the radiation before entry into the sterile room.

On account of the complex light-scattering conditions in the interior it is additionally necessary to make conveying channels for the closures satisfactory in order to prevent scattered radiation. As a result, a change of these channels, which is necessary in particular in the case of plants which have to apply all kinds of different container closures to containers, is time-consuming and this leads to an increased loss of production time for the operator of the plant and reduces the productivity of the plant. In addition, it is also not possible to transfer known apparatus for cleaning containers to apparatus for cleaning container closures, since although on the one hand container closures do not require disinfection over large areas, such as for example container walls, on the other hand in the region of the thread they have a very complex structure which is thus difficult to clean. For the reasons described, the cleaning of container closures by means of UV radiation in particular in sterile rooms and in particular in sterile applications has hitherto not been usual, but the predominant practice has been to fall back on the use of disinfectants.

SUMMARY OF THE INVENTION

The object of the present invention is therefore to make available an apparatus and a method which allow a simplification of the apparatus known from the prior art. In particular, an improved accessibility of the conveying apparatus for the container closures is to be achieved. In addition, it should be easier for changes of these conveying apparatus to be carried out.

An apparatus according to the invention for sterilizing container closures has a conveying device which conveys the container closures along a pre-determined conveying path. Furthermore, the apparatus has a housing which surrounds the conveying device at least at a distance, as well as a light source which acts upon the container closures with ultraviolet radiation during the conveying along the conveying path. According to the invention the light source is arranged outside the housing and the ultraviolet radiation is directed into the interior of the housing and onto the container closures or is guided into the interior of the housing. The housing surrounds the apparatus according to the invention at least in part i.e. according to the invention the apparatus can be situated in a clean or sterile room just as the housing can be formed by a machine protection known to the person skilled in the art.

It is thus proposed that the light source itself should be arranged outside a housing or outside a sterile room respectively. In this way, the light source, such as in particular a UV lamp, is easily accessible for repair and assembly purposes. Furthermore, in contrast to the prior art, an aeration for this light source can likewise be provided at the same time outside the housing, so that undesired air movements do not occur in the interior of the housing.

Furthermore, it is also not necessary for the conveying device or closure channel to be enclosed and to take up space, so that it is easier to carry out a change of the channel. The apparatus according to the invention can thus also easily be retrofitted in existing plants, and is also not dependent upon the sizes of the closure channels. Furthermore, the problem known from the prior art, that heating of the closures by the waste heat of the light source can occur during a stoppage of the plant is minimized. In the event of a stoppage of the plant or a defect the use of process air for cooling the light sources can also be omitted.

Whereas different special designs are necessary in the prior art for different light sources, it is now possible for the light source (not critical in its positioning) to be arranged with standard components.

It is preferable for the apparatus to have a light conductor which directs the radiation from the light source to the container closures. In this way it is possible for the light also to be conveyed from the light source to the container closures by way of curved or occupied paths. It is also possible for the screening outlay to be reduced by the use of light conductors. It would also be possible, however, for the light source to aim the light directly onto the sterilizing container closures.

Furthermore, a coupling apparatus is provided in order to couple the ultraviolet radiation into the light conductor This coupling apparatus is preferably a lens or a prism.

In a further advantageous embodiment the conveying device is a conveying rail or conveying channel, along which the container closures preferably slide under the action of gravity. In this case it is particularly preferable for the conveying rail to form a back-up area inside which the container closures are conveyed lying one immediately after the other. In contrast to conveying devices for containers which are usually conveyed in a clock-timed manner and at pre-determined intervals from one another, it is proposed in this case that the container closures should be backed up in the region of a back-up path, in order to achieve a relatively slow movement of the container closures in this way so that they can be sterilized efficiently even at critical places such as for example the region of their internal thread. In contrast to apparatus which sterilize containers, the closures are preferably not gripped individually.

In a further advantageous embodiment the apparatus has an outlet device which aims the light radiation directly onto the container closures. In this case, in particular those regions of the container closures which comprise the threads are sterilized. It is preferable for the conveying device to be housed only in the region of this outlet device. It would also be possible, however, for the outlet device—which is also for example a lens or a prism—to be brought so close to the containers that the housing can be omitted completely.

In this case the conveying rail preferably guides the container closures in such a way that the inner region thereof (i.e. also the thread) is facing the outlet device.

In a further advantageous embodiment the outlet device has a scattering device which scatters the light reaching the container closures. In this way, it is possible for relatively large areas of the container closures to be sterilized. It is particularly preferred for this scattering device likewise to be a prism. The radiation can nevertheless, however, be diverted in particular onto the critical zones of the container closures.

In a further advantageous embodiment the apparatus has a plurality of outlet devices by which beams originating from the same light source are aimed at the containers, these outlet devices being arranged at different points on the conveying path of the containers. In this way, it is possible in a particularly convenient manner for different areas of the conveying closures to be sterilized. In this case, although sterilization takes place at different areas of the conveying path, use can be made of the same light source. In this way, it is possible for example for the container closures to be sterilized with a first outlet device on their external periphery and for the internal area of the container closures to be sterilized with a further outlet device. In this case it is preferable for the light conductors and, in particular but not exclusively, glass-fibre cables, to be provided between all the outlet devices and the light source.

It is preferable for the container closures to be conveyed inside a sterile room and for this sterile room to be surrounded by the housing. The present invention is particularly suitable for sterile applications in particular since in applications of this type the size of the areas inside the sterile room is also to be kept small. In this case the housing preferably seals the sterile room off from the surroundings completely. In addition, it is possible for different pressure ratios from the surroundings to prevail in the sterile room.

In a further advantageous embodiment the conveying device is not screened off inside the housing at least in part. This means that in this region the conveying device or the channel respectively is very easily accessible or is very easy to change respectively.

The present invention further relates to a plant for closing containers with container closures, which has an apparatus of the type described above and a closure device arranged downstream with respect to this apparatus for attaching the container closures to the containers. This closure device preferably has one or more closure elements which screw the container closures onto the containers or attach them in some other way.

It is preferable for the closure device for closing the containers to be arranged inside the sterile room in which the conveying device for the container closures is also provided. Furthermore, the plant preferably has a further sterilization unit for sterilizing the containers This further unit can also be housed inside the sterile room (in which the conveying device is also provided). In this case it is possible for the containers themselves likewise to be sterilized with UV radiation. In addition it would be possible for the same light source to be used for sterilizing the containers as for sterilizing the container closures.

The present invention further relates to a method of sterilizing container closures, in which the container closures are conveyed inside a housing along a predetermined conveying path and during this conveying are acted upon by a light source with ultraviolet radiation to sterilize them. According to the invention the radiation is produced outside the housing and is introduced into the housing. It is preferable for the container closures to be attached to containers or to be screwed onto them after they have been sterilized.

It is preferable for the container closures to be acted upon with ultraviolet radiation at a plurality of areas along the conveying path.

BRIEF DESCRIPTION OF THE DRAWINGS

Further advantages and embodiments may be seen in the accompanying drawings. In the drawings

DETAILED DESCRIPTION OF THE INVENTION

Figure 1:
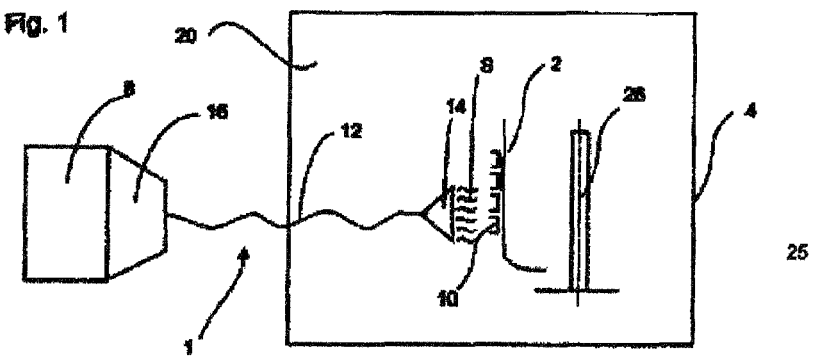
FIG. 1 is a diagrammatic illustration to explain the invention.

FIG. 1 is a diagrammatic illustration of an apparatus 1 according to the invention. This apparatus has a housing 4, inside which a clean room or a sterile room 20 respectively is formed. It is preferable for this sterile room 20 to be closed off in a substantially air-tight or gas-tight manner with respect to the surroundings 25. A conveying device 2, by means of which the container closures 10 are conveyed, is provided in the interior of the housing 4. In this case, as shown in FIG. 1, the container closures are conveyed in such a way that the openings thereof can be irradiated directly by ultraviolet radiation S.

The reference number 8 designates a light source which irradiates the ultraviolet radiation into the sterile room 20 by way of a prism and a light conductor 12. In this case openings (not shown), through which the light conductor is guided into the interior of the housing 4, are provided in the housing 4. It is preferable for sealing devices also to be provided which seal off the transition between the light conductor 12 and the corresponding housing wall.

The reference number 14 designates an outlet apparatus which aims the radiation arriving from the light conductor 12 in a planar manner onto the container closures 10, in which case, as mentioned above, the inner regions of the container closures 10 are facing this outlet device 14.

Figure 2:
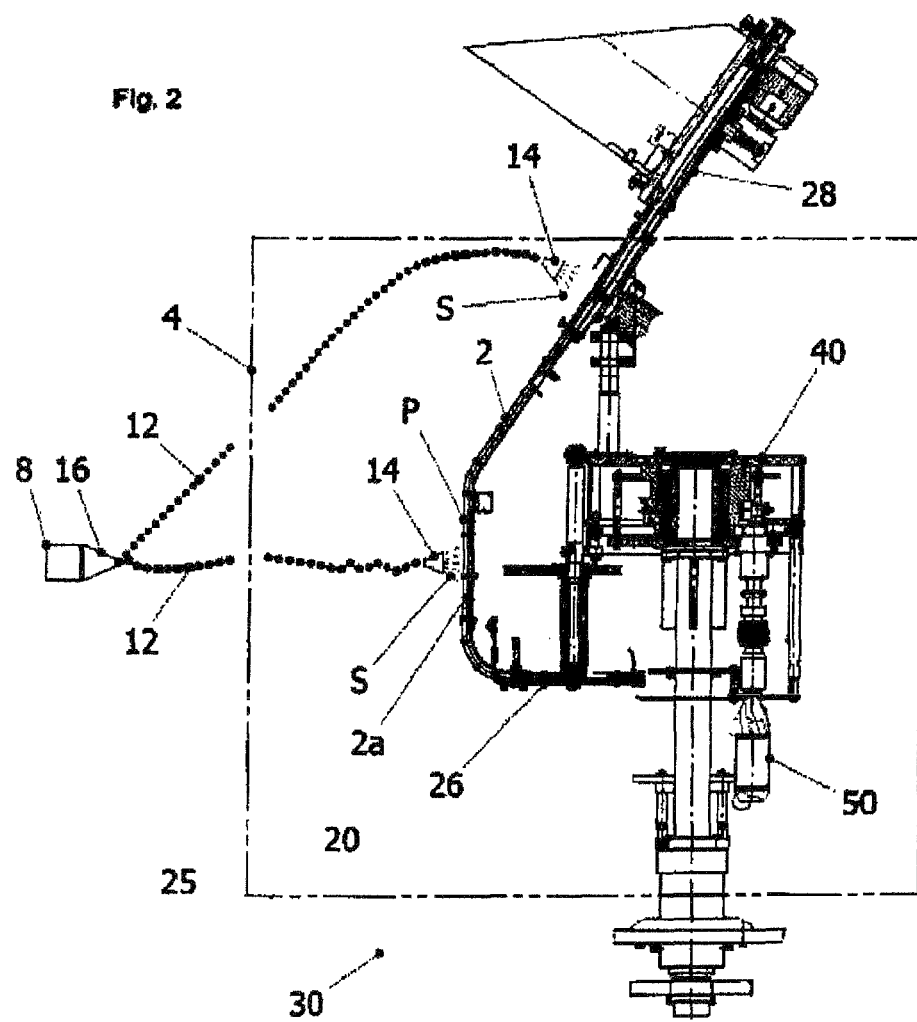
FIG. 2 is a detailed illustration of an apparatus according to the invention.

FIG. 2 is a detailed illustration of an apparatus 1 according to the invention or a plant 30 for closing containers 50 with container closures. It will be recognized in this case that the conveying device 2 is designed in the form of a channel, inside which the closures (not shown) can slide. In this case a vertical portion 2a of this channel is provided, inside which the closures can slide vertically downwards. It is preferable for a back-up path also to be provided in this region, so that the container closures 10 back up here. According to the invention, instead of a vertical conveying by gravity it is also possible for any known conveying method to be used for conveying the closures, such as for example a pneumatic conveying through sterile air or devices for the mechanical advance of the closures Furthermore, as shown in FIG. 2, two outlet devices 14 are provided which are arranged in different regions of the conveying device 2. The reference number 28 designates a sorting unit, inside which the container closures are sorted and are also arranged in one plane for example. In this region an irradiation with UV radiation is likewise particularly well suited for achieving sterilization of the container closures.

The reference P designates the conveying path of the container closures. It will be noted that the two outlet devices 14 are supplied by the same light source which is arranged outside the housing 4. The reference number 16 designates a prism which is used for light concentration.

The conveying rail is followed by an image-recording device or inspection device 22 which records images of the container closures. The reference number 40 designates as a whole a closure device which attaches the container closures to containers 50 to be closed. Reference is made to the fact that the closure device 40 is also arranged inside the housing 4.

The applicants reserve the right to claim all the features disclosed in the application documents as being essential to the invention, insofar as they are novel either individually or in combination as compared with the prior art.

The invention claimed is:

1. An apparatus for sterilizing container closures with a conveying device which conveys the container closures along a pre-determined conveying path (P), with a housing which surrounds the conveying device at least locally, and with an ultraviolet light source which acts upon the container closures with ultraviolet radiation during the conveying along the conveying path (P), wherein the ultraviolet light source is arranged outside the housing and the ultraviolet radiation (S) is directed into the interior of the housing, further comprising an outlet device which aims ultraviolet radiation from the ultraviolet light source directly onto the container closures, wherein the outlet device is a lens or prism.

2. An apparatus for sterilizing container closures with a conveying device which conveys the container closures along a pre-determined conveying path (P), with a housing which surrounds the conveying device at least locally, and with an ultraviolet light source which acts upon the container closures with ultraviolet radiation during the conveying along the conveying path (P), wherein the ultraviolet light source is arranged outside the housing and the ultraviolet radiation (S) is directed into the interior of the housing, further comprising an outlet device which aims ultraviolet radiation from the ultraviolet light source directly onto the container closures, wherein the container closures are conveyed inside a sterile room and this sterile room is surrounded by the housing.

3. An apparatus for sterilizing container closures with a conveying device which conveys the container closures along a predetermined conveying path (P), with a housing which surrounds the conveying device at least locally, and with an ultraviolet light source which acts upon the container closures with ultraviolet radiation during the conveying along the conveying path (P), wherein the ultraviolet light source is arranged outside the housing and the ultraviolet radiation (S) is directed into the interior of the housing, further comprising an outlet device which aims ultraviolet radiation from the ultraviolet light source directly onto the container closures, a light conductor which directs the ultraviolet radiation from the ultraviolet light source to the container closures, and coupling apparatus for coupling the ultraviolet radiation into the light conductor.

4. The apparatus according to claim 3, wherein the conveying device is a conveying rail, along which the container closures slide under the action of gravity.

5. The apparatus according to claim 4, wherein the conveying rail forms a back-up area, inside which the container closures are conveyed lying one immediately against the other.

6. The apparatus according to claim 3, wherein the conveying device is an air conveyor.

7. The apparatus according to claim 3, wherein the conveying device has a mechanical advancing apparatus.

8. The apparatus according to claim 3, wherein a scattering device, which scatters ultraviolet light arriving at the container closures, is arranged on the outlet device.

9. The apparatus according to claim 3, further comprising a plurality of outlet devices by which ultraviolet radiation originating from the ultraviolet light source is aimed at the container closures, wherein the plurality of outlet devices are arranged at different points on the conveying path of the container closures.

10. The apparatus according to claim 9, wherein a first outlet device sterilizes the container closures on their external periphery and an additional outlet device sterilizes an internal area of the container closures.

11. The apparatus according to claim 3, wherein the conveying device is not screened off inside the housing at least locally.

12. The apparatus according to claim 3, wherein the coupling apparatus is a lens or a prism.

13. The apparatus according to claim 3, wherein the conveying device is only housed in the region of the outlet device.

14. The apparatus according to claim 3, wherein the conveying device guides the container closures in such a way that an inner region of the container closures faces the outlet device.

15. The apparatus according to claim 3, wherein the container closures are acted upon with the ultraviolet radiation at a plurality of areas along the conveying path.

16. The apparatus according to claim 3, further comprising a sorting unit, inside which the container closures are sorted and are also arranged in one plane, and, wherein sterilization by the ultraviolet radiation is achieved.

17. A plant for closing containers with container closures with an apparatus according to claim 3, and a closure device arranged downstream with respect to an apparatus for attaching the container closures to the containers.

18. The plant according to claim 17, wherein the closure device is arranged inside a sterile room.

19. A method of sterilizing container closures using the apparatus of claim 3, wherein the container closures are conveyed inside a housing along a pre-determined conveying path (P) and during this conveying the container closure are acted upon by a light source with ultraviolet radiation to sterilize them, wherein the ultraviolet radiation is produced outside the housing and is introduced into the housing.

20. The method according to claim 19, wherein the container closures are attached to containers after they have been sterilized.

* * * * *